United States Patent
Stokes et al.

(10) Patent No.: US 7,254,986 B2
(45) Date of Patent: Aug. 14, 2007

(54) SENSOR DEVICE FOR DETECTION OF DISSOLVED HYDROCARBON GASES IN OIL FILLED HIGH-VOLTAGE ELECTRICAL EQUIPMENT

(75) Inventors: Edward B. Stokes, Charlotte, NC (US); Peter M. Sandvik, Guilderland, NY (US); Vinayak Tilak, Watervliet, NY (US); Jeffrey B. Fedison, Niskayuna, NY (US); Elena Babes-Dornea, Pierrefonds (CA); Renyan Qin, Dollard-des-Ormeaux (CA); James W. Rose, Guilderland, NY (US); Stanton E. Weaver, Northvale, NJ (US)

(73) Assignee: General Electric Company, Schenectady, NY (US)

( * ) Notice: Subject to any disclaimer, the term of this patent is extended or adjusted under 35 U.S.C. 154(b) by 603 days.

(21) Appl. No.: 10/319,359

(22) Filed: Dec. 13, 2002

(65) Prior Publication Data
US 2004/0112764 A1    Jun. 17, 2004

(51) Int. Cl.
*G01N 7/00* (2006.01)
*G01N 9/00* (2006.01)
(52) U.S. Cl. ............... 73/31.06; 204/400; 204/424; 204/426; 204/431
(58) Field of Classification Search ............... 73/31.06; 204/400, 424–435
See application file for complete search history.

(56) References Cited

U.S. PATENT DOCUMENTS

| | | | | | |
|---|---|---|---|---|---|
| 3,951,161 | A | * | 4/1976 | Rohrback et al. ............... 137/3 |
| 4,347,732 | A | * | 9/1982 | Leary ........................ 73/31.05 |
| 5,285,084 | A | * | 2/1994 | von Windheim et al. ..... 257/77 |
| 5,362,975 | A | * | 11/1994 | von Windheim et al. ..... 257/76 |
| 5,417,821 | A | * | 5/1995 | Pyke .......................... 205/775 |

(Continued)

FOREIGN PATENT DOCUMENTS

CA    2235021    10/1999

(Continued)

OTHER PUBLICATIONS

Svenningstorp, Henrik, et al., *MISiC Schottky Diodes as $NO_x$ Sensors in Simulated Exhausts*, EUROSENSORS XIII, Sep. 12-15, pp. 501-504 (1999).

(Continued)

*Primary Examiner*—Hezron Williams
*Assistant Examiner*—Samir M. Shah
(74) *Attorney, Agent, or Firm*—Cantor Colburn LLP

(57) ABSTRACT

A multi-gas sensor device for the detection of dissolved hydrocarbon gases in oil-filled electrical equipment. The device comprising a semiconductor substrate, one or more catalytic metal gate-electrodes deposited on the surface of the semiconductor substrate operable for sensing various gases, and an ohmic contact deposited on the surface of the semiconductor substrate. The semiconductor substrate comprises one of GaN, SiC, AlN, InN, AlGaN, InGaN and AlInGaN. A method for sensing gas in an oil-filled reservoir of electrical equipment, comprising providing a sensor device, immersing the sensor device in the oil-filled reservoir, allowing the gases emitted from the oil to interact with the one or more catalytic metal gate-electrodes, altering the gas as it contacts the catalytic metal gate-electrodes and altering the sensitivity of the sensor.

34 Claims, 6 Drawing Sheets

U.S. PATENT DOCUMENTS

| | | | |
|---|---|---|---|
| 5,591,321 A | | 1/1997 | Pyke |
| 5,656,827 A | * | 8/1997 | Kang et al. ............... 257/76 |
| 5,979,423 A | | 11/1999 | Poindexter et al. |
| 6,041,643 A | * | 3/2000 | Stokes et al. ............ 73/31.06 |
| 6,109,094 A | * | 8/2000 | Baranzahi et al. ...... 73/31.06 |
| 6,155,100 A | * | 12/2000 | Stokes et al. ............ 73/31.06 |
| 6,182,500 B1 | * | 2/2001 | Stokes et al. ............ 73/31.06 |
| 6,202,473 B1 | * | 3/2001 | Stokes et al. ............ 73/31.06 |
| 6,268,560 B1 | | 7/2001 | Zuppero et al. |
| 6,291,838 B1 | * | 9/2001 | Hunter ...................... 257/76 |
| 6,298,710 B1 | | 10/2001 | Samman et al. |
| 6,433,356 B1 | * | 8/2002 | Cahen et al. ............... 257/40 |
| 6,634,213 B1 | * | 10/2003 | O'Connor et al. ....... 73/31.06 |
| 6,649,823 B2 | | 11/2003 | Zuppero et al. |
| 6,700,056 B2 | | 3/2004 | Zuppero et al. |
| 7,053,425 B2 | * | 5/2006 | Sandvik et al. ............ 257/253 |
| 7,156,967 B2 | * | 1/2007 | Hotta et al. ............... 204/429 |
| 7,157,054 B2 | * | 1/2007 | Toyoda et al. .............. 422/88 |
| 2002/0152798 A1 | * | 10/2002 | Leverrier et al. ......... 73/31.05 |
| 2004/0069224 A1 | * | 4/2004 | Lin et al. .................. 118/715 |

FOREIGN PATENT DOCUMENTS

| | | |
|---|---|---|
| DE | 100 31 549 A1 | 1/2002 |
| EP | 0 280 540 | 2/1988 |
| EP | 280540 A2 * | 8/1988 |
| EP | 1 079 229 | 8/1999 |
| EP | 1 179 730 | 8/2001 |
| WO | WO 95/12811 | 5/1995 |

OTHER PUBLICATIONS

Spetz, A. Lloyd, et al., *Si and SiC Based Field Effect Devices*, TAFT, 2000, Nancy, France, pp. 27-30 (Mar. 2000).

Mattsson, L. Unéus, et al., *Monitoring of Hot Flue Gases by an E-Nose Equipped with SiC Based Sensors and Metal Oxide Sensors*, Editors, J.W. Gardner and K.C. Persaud, Institute of Physics Publishing, ISOEN2000, Brighton, pp. 291-296 (Jul. 2000).

Spetz, A. Lloyd, et al., *MISiCFET Chemical Gas Sensors for High Temperature and Corrosive Environment Applications*, Proc. ICSCRM2001, Tsukuba, Japan, Oct. 28-Nov. 2, 2001, accepted.

Hunter, Gary, et al., *Microfabricated Chemical Sensors for Space Health Monitoring Applications*, American Institute of Aeronautics and Astronautics, AIAA 2001-4689, pp. 1-12.

Spetz, A. Lloyd, et al., *MISiCFET Chemical Gas Sensors for High Temperature and Corrosive Environment Applications*, Materials Science Forum vols. 389-393 pp. 1415-1418 (2002).

Kokubun, Yoshihiro, et al., *Effects of Ambient Gases on Current-Voltage Characteristics of Pt-GaN Schottky Diordes at High Temperatures*, Jpn. J. Appl. Phys. vol. 40, pp. L663-L665 (2001).

Shields, V.B., et al., *A Variable Potential Porous Silicon Carbide Hydrocarbon Gas Sensor*, Inst. Phys. Conv. Ser. No. 142; Chapter 7, pp. 1067-1070 (1996).

Lee, Dae-Sik, et al., *GaN Thin Film Gas Sensors*, IPAP Conf. Series 1 pp. 919-922.

Luther, B.P., et al., *High Temperature Pt Schottky Diode Gas Sensors On N-Type GaN*, ELSEVIER, Sensors and Actuators B Chemical 56, pp. 164-168 (1999).

Samman, A., et al., *Platinum-Aluminum Nitride-Silicon Carbide Diodes As Combustible Gas Sensors*, Journal of Applied Physics, vol. 87, No. 6, pp. 3101-3107 (Mar. 15, 2000).

Serina, F., et al., *Pd/AlN/SiC Thin-Film Devices for Selective Hydrogen Sensing*, Applied Physics Letters, vol. 79, No. 20, pp. 3350-3352 (Nov. 12, 2001).

Eickhoff, M., et al., *Novel Sensor Applications of Group-III Nitrides*, (Presented at 112.1 Fall 2001 MRS).

Schalwig, J., et al., *Hydrogen Response Mechanism of PT-GaN Schottky Diodes*, Applied Physics Letters, vol. 80, No. 7, pp. 1222-1224 (Feb. 18, 2002).

Stutzmann, M., et al., *GaN-Based Heterostructures for Sensor Applications*, ELSEVIER, Diamond and Related Materials, 11, pp. 886-891 (2002).

Pyke, Stephen, et al., *Gallium Nitride Integrated Gas/Temperature Sensors for Fuel Cell System Monitoring for Hydrogen and Carbon Monoxide*, Proceedings of the 2002 U.S. DOE Hydrogen Program Review, NREL/CP-610-32405 pp. 1-11.

Pearton, S.J., et al., *New Applications for Gallium Nitride*, Materialstoday, Jun. 2002 ISSN: 1369 7021 Elsevier Science Ltd. pp. 24-31 (Jun. 2002).

Schalwig, J., et al., *Gas Sensitive GaN/AlGaN-Heterostructures*, ELSEVIER, Sensors and Actuators B 6786 pp. 1-6 (2002).

* cited by examiner

SENSOR DEVICE FOR DETECTION OF DISSOLVED HYDROCARBON GASES IN OIL FILLED HIGH-VOLTAGE ELECTRICAL EQUIPMENT

BACKGROUND OF THE INVENTION

1. Field of the Invention

The present invention relates generally to the field of gas sensors. More particularly, the present invention relates to semiconductor gas sensors made from wide bandgap materials such as gallium nitride (GaN) and silicon carbide (SiC) that are effective at providing continuous or discrete measure of gas levels resulting from degradation processes in insulating oil in oil-filled high-voltage electrical equipment.

2. Description of the Related Art

Gas sensors have been used in the detection of particular symptomatic gases in oil-filled electrical equipment. Faults in oil-filled transformers, for example, may include arcing (electrical), corona discharge (electrical), low energy sparking (electrical), severe overloading (electrical), pump motor failure (electrical and thermal) and overheating (electrical and thermal) in an insulation system. Faults may generate undesirable gases, such as hydrogen ($H_2$), acetylene ($C_2H_2$), ethylene ($C_2H_4$), methane ($CH_4$), ethane ($C_2H_4$), carbon monoxide (CO) and carbon dioxide ($CO_2$). These fault conditions result in a malfunctioning transformer or may indicate an impending malfunction, which, if not corrected, may lead to failure of the transformer. A statistical correlation exists between transformer malfunction and fault gases generated by the transformer. Accordingly, if the accurate detection of potentially dangerous gases in a transformer is achieved, possible malfunction and failure of the transformer can be addressed and often avoided.

The principles described previously for oil filled transformers may also be applied to other pieces of oil filled equipment or facilities, in which high electrical fields or temperature oscillations cause the oil to break down into its potentially flammable constituents over time. One example of such equipment includes x-ray tubes used in medical applications. X-ray tubes supply x-rays used in medical assessments of bone or tissue structure. These tubes, much like transformers, use oil to both insulate and cool internal electrical components. Gas sensors fabricated from GaN or SiC would provide a non-intrusive method for maintaining such equipment regularly, minimizing down-time and avoiding catastrophic fault conditions.

With respect to hydrogen, power transformers expose insulating oil to high electric fields that break down the oil over time. Hydrogen gas and hydrogen bearing compounds are given off, indicating the need for preventative maintenance. If this need goes unheeded, it may lead to the build-up of flammable hydrogen gas in the system, which if ignited, may lead to catastrophic failure. Current detection systems for hydrogen include oil sampling and chromatographic analysis, single gas sensors and person-operated units. These conventional approaches are time consuming, expensive, offer incomplete information, and in some cases are only performed periodically throughout the year.

The ability of sensors to identify a target gas depends on several factors. These factors include the sensitivity of the sensor to other interfering gases and vapors, and a concentration of the target gas. The ability to resolve the target gas from other gases is called the selectivity. There are very few known sensors that are highly selective where a sensor has greater than about a tenfold difference in gas detection between sensing states and non-sensing states. Further, within these very few sensors there are even fewer that are relatively reliable to accurately detect individual gases.

Current semiconductor gas sensor technology may make use of $Si/SiO_2$ as materials on which a gas is sensed. Others may make use of $SnO_2$ or other oxides, however, in the case of $SnO_2$, these devices typically require a heater to increase their temperature in excess of 200 deg C. in order to make them sensitive enough to be useful. While these sensors are mass producible, they often fail in outdoor environments where the temperature fluctuates. Temperature fluctuations may lead to drift in response to gaseous environments over time, which means that the change in electrical response to the same gas will differ over time, thus the sensor system will require temperature correction in order to track quantitative changes. Even small changes in a temperature range, such as about −40 to about 130 deg F., are enough to cause such drift over time. Drift is most noticeable in Si devices, making these devices ineffective in such ambient settings. In order to minimize drift, the Si-based sensors often require heating to a temperature of up to about 150 deg C. in order to return the sensors to nominal operating conditions. Despite the heating, drift over time still occurs due to surface states formed from oxides and other elements on the surface of the sensors.

U.S. Pat. Nos. 6,041,643, 6,155,100, 6,182,500 and 6,202,473 all issued to Stokes et al., incorporated herein by reference, describe a gas sensor for determining the presence of at least one gas in a gaseous environment. The gas sensor includes a semiconductor substrate, a thin insulator layer disposed on the semiconductor substrate, a catalytic metallic gate disposed on the thin insulator layer and a chemically modified layer disposed on the catalytic metal gate. The chemically modified layer includes a material that protects the sensor from corrosive gases and interference from at least one of foreign matter and water, alters at least one of surface chemical properties and surface physical properties of the sensor, and passes only a designated gas therethrough.

What is needed is a more robust material system for addressing material issues and eliminating drift. What is further needed is a high temperature, harsh environment capable gas sensor that outperforms conventional solid-state sensors that use semiconductor materials such as Si.

BRIEF SUMMARY OF THE INVENTION

In various embodiments, the present invention provides semiconductor gas sensors made from wide bandgap materials such as gallium nitride (GaN) and silicon carbide (SiC) that are effective at providing a continuous measure of gas levels in oil-filled high-voltage electrical equipment. These materials are more robust than silicon (Si) and operate well in a wide range of ambient environments. These material systems provide chemically stable, repeatable responses in wide temperature ranges and harsh environments and are effective up to about 450 deg C. over a wide range of pressures. The term harsh environment is meant to include temperatures above about 150 deg C., where Si devices degrade and suffer significant reliability issues. Harsh environments may also include high pressures, high vibrations, a combination therein or other.

In one embodiment, the present invention provides a multi-gas sensor device comprising a semiconductor substrate, one or more catalytic metal gate-electrodes deposited on the surface of the semiconductor substrate, and an ohmic contact deposited on the surface of the semiconductor substrate. Each catalytic metal-gate electrode may be operable for sensing a different gas. The multi-gas sensor device operates in a gaseous environment, such as immersed in electrically non-conductive oil containing dissolved gases.

In another embodiment, the semiconductor substrate is selected from the group consisting of group III, IV and V materials, such as GaN, SiC, AlN, AlGaN, InN, InGaN and AlInGaN. The one or more catalytic metal gate-electrodes comprise platinum, palladium, iridium, ruthenium, nickel, copper, rhodium, molybdenum, iron, cobalt, titanium, vanadium, tantalum, tungsten, chromium, manganese, gold, silver, aluminum, palladium:silver, tin, osmium, magnesium, zinc, alloys of these materials and combinations of these materials.

In a further embodiment, the gases comprise hydrogen, hydrogen-bearing, oxygen, oxygen-bearing and others, and are a result of the degradation of oil caused by heat and electric fields.

In a still further embodiment, the present invention provides a gas sensor device comprising a semiconductor substrate, a catalytic metal gate-electrode deposited on the semiconductor substrate, an ohmic contact deposited on the semiconductor substrate, a passivation layer operable for increasing the selectivity of the device to a gas and a heating mechanism. The passivation layer may comprise silicon nitride, silicon dioxide, silioxynitride, hafnium oxide, titanium oxide, indium doped titanium oxide, aluminum oxide, gallium oxide, or alloys or combinations of these materials.

In a still further embodiment, a method is provided for detecting various gases. The method comprises providing a sensor device, immersing the sensor device in an oil-filled environment, allowing the oil-filled environment to interact with the one or more catalytic metal gate-electrodes, altering the various gases as they contact the catalytic metal gate-electrodes, the altering comprising at least one of atomically and molecularly altering chemical structure of the various gases, and altering the sensitivity of the sensor device. The sensor device comprises a semiconductor substrate, one or more catalytic metal gate-electrodes deposited on the surface of the semiconductor substrate, wherein each of the one or more catalytic metal gate-electrodes is operable for sensing a different gas, and an ohmic contact deposited on the surface of the semiconductor substrate.

In a still further embodiment, a method for sensing various gases comprises providing a sensor device, immersing the sensor device in the oil-filled reservoir, allowing the oil to interact with the one or more catalytic metal gate-electrodes, altering the gas as it contacts the catalytic metal gate-electrodes, the altering comprising at least one of atomically and molecularly altering chemical structure of the gas, and altering the sensitivity of the sensor device. The sensor device comprises a semiconductor substrate, one or more catalytic metal gate-electrodes deposited on the surface of the semiconductor substrate, an ohmic contact deposited on the surface of the semiconductor substrate, a passivation layer operable for increasing the selectivity of the device to the gas and a heating mechanism for increasing the sensor device response to the gases.

In a still further embodiment, a method for sensing various gases comprises providing a sensor device, immersing the sensor device in the oil-filled reservoir, allowing only the gases in the oil to interact with the one or more catalytic metal gate-electrodes by using a protective, selectively porous membrane material, altering the gas as it contacts the catalytic metal gate-electrodes, the altering comprising at least one of atomically and molecularly altering chemical structure of the gas, and altering the sensitivity of the sensor device. The sensor device comprises a semiconductor substrate, one or more catalytic metal gate-electrodes deposited on the surface of the semiconductor substrate, an ohmic contact deposited on the surface of the semiconductor substrate, a passivation layer operable for increasing the selectivity of the device to the gas, a heating mechanism for increasing the sensor device response to the gases, and a protective gate material such as a selectively porous membrane which allows only certain gases to pass through it to the semiconductor device and its catalytic metals.

BRIEF DESCRIPTION OF THE DRAWINGS

A variety of specific embodiments of this invention will now be illustrated with reference to the Figures. In these Figures, like elements have been given like numerals.

DETAILED DESCRIPTION OF THE INVENTION

As required, detailed embodiments of the present invention are disclosed herein, however, it is to be understood that the disclosed embodiments are merely exemplary of the invention that may be embodied in various and alternative forms. Specific structural and functional details disclosed herein are not to be interpreted as limiting, but merely as a basis for the claims as a representative basis for teaching one skilled in the art to variously employ the present invention. Throughout the drawings, like elements are given like numerals. The systems described below apply to sensing levels of gases in insulating oil in oil-filled high-voltage electrical equipment, however, in principle also apply to any system that benefits from gas sensing.

The present invention will now be described with a sensor operating in electrically non-conductive oil, such as in power transformer or x-ray tube oil reservoirs, which are merely example applications for the sensor. The sensor may also operate in air and form part of an exhaust gas monitoring system for gas turbines, diesel locomotives and aircraft engines, where the detection of gases is desirable. The sensor, its operation and the detection of hydrogen gas are merely exemplary and are not meant to limit the invention.

Figure 1:
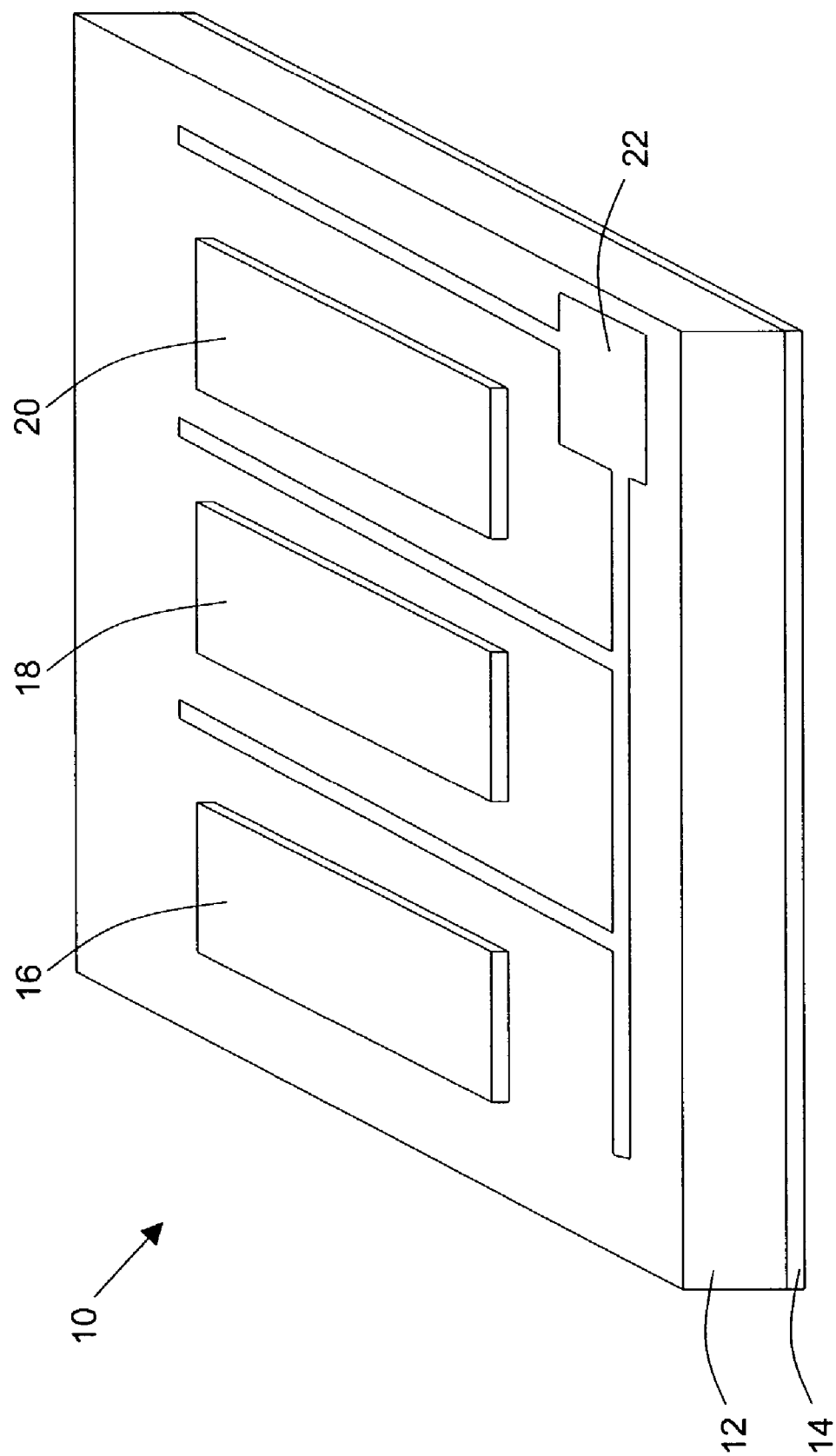
FIG. 1 is a schematic diagram illustrating a multi-gas sensor device comprising three gate-electrodes in accordance with an exemplary embodiment of the present invention.

Referring now to FIG. 1, a gas sensor device 10 for gas-in-oil detection in high power electrical equipment/transformers is schematically shown. The sensor device 10 may make use of an induced electrical field at the surface of the device 10 from hydrogen ions, and/or hydrogen molecules that are polarized. The polarization may be detected by measuring current-voltage characteristics, or by measuring the capacitance of the device 10. This may be accomplished using several configurations such as a diode (Schottky) with a catalytic gate-electrode, a capacitor or a field effect transistor (FET) of different configurations, which use a catalytic metal as the gate.

The gas sensor device 10 comprises a multi-electrode gas sensor fabricated on a semiconductor layer 12. The semiconductor layer 12 is epitaxially grown over a substrate layer 14. The substrate layer 14 comprises an inorganic crystallization growth substrate, such as sapphire, silicon, silicon carbide, aluminum oxide, aluminum nitride, gallium nitride, gallium arsenide, aluminum gallium nitride, lithium gallate or any other substrate capable of supporting crystal growth on at least a portion of exposed area of the surface of the substrate 14.

The device 10 comprises several electrode metals, each having a different sensitivity to different gases, making it a multi-gas sensor. Each electrode response is proportional to the concentration of a target gas, and the response to the target gas is high enough to overcome background noise. In one embodiment, the present invention comprises a two or more terminal solid-state gas sensor device fabricated from a group-III/IV/V-based semiconductor epitaxial layer 12 onto which thin metal catalytic gate-electrodes 16, 18, 20 (e.g., Schottky contacts) are deposited. FIG. 1 shows three gate-electrodes for exemplary purposes, however, the sensor device 10 of the present invention may be practiced using two or more gate-electrodes incorporated into a single large device, however, an array of different devices is also envisioned. Etching may be used to isolate gate-electrode components. A potential change of the gate-electrode 16, 18, 20 leads to a change in the electronic equilibrium in the underlying n- or p-type semiconductor layer 12. The sensor device further comprises a thick metallic ohmic contact 22 deposited on the semiconductor layer 12.

The gate-electrodes 16, 18, 20 serve as catalysts for a polarization layer from a set of gases (hydrogen, hydrogen bearing, oxygen, oxygen bearing, among others).

The metallic gate-electrodes 16, 18, 20 comprise a suitably thick layer of material of an appropriate corrosive-resistant gate material. For example, the materials of the metallic gate-electrodes 16, 18, 20 comprise an appropriate metallic material, such as, but not limited to at least one of: platinum, palladium, iridium, ruthenium, nickel, copper, rhodium, molybdenum, iron, cobalt, titanium, vanadium, tantalum, tungsten, chromium, manganese, gold, silver, aluminum, palladium:silver, tin, osmium, magnesium, zinc, alloys of these materials, and combinations of these materials.

The different catalytic metals possess different sensitivities to various gases of interest, making the single sensor device 10 operable for detecting several gaseous elements, distinguishing between them and determining concentrations. The catalytic gate-electrodes 16, 18, 20 have a thickness in a range preferably between about 5 nm to about 100 nm, more preferably from about 8 nm to about 50 nm, and even more preferably about 20 nm in thickness. The thickness of the metallic gate-electrodes 16, 18, 20 depend on the intended use of the sensor device 10. The level of sensitivity for each gas may be different for each particular gate material. The sensor device 10 may be tuned to a particular gas by virtue of the particular gate material chosen, and/or by modifying the surface geometry and/or area in which each particular metal is placed.

For high temperature applications, the gas sensor device 10 may be made up of semiconductor materials from group-III, IV and V materials. The most common alloys that may be used in the practice of the present invention comprise binary alloys such as GaN, InN, SiC and AlN. Ternary alloys, such as AlGaN and InGaN, and quaternary alloys, such as AlInGaN, may also be considered for use in the present invention. These alloys, such as GaN and SiC, are both resistant to harsh environments and capable of operation at high temperatures, such as over about 150 deg C. In addition, the chemical inertness of GaN and SiC gives them a high resistance to etching and degradation, even in the presence of strong acids or bases. The wide bandgaps of GaN and SiC make these materials ideal for the harsh environments described above. Different semiconductor materials may be combined to achieve differing responses and sensitivities in arrays or single devices.

The sensor device 10 provides for the continuous, accurate and repeatable detection of potentially hazardous gases in an ambient environment ranging from about −40 to about 130 deg F. without sensor drift, which is a common problem in currently used Si sensor technology. Different temperatures may be used with various diodes or on an array or single diode for temperature dependent variance in sensitivity to different gases.

A low-resistance ohmic contact 22 is necessary in the successful implementation of the multi-gas sensor device 10. For example, a Ti/Al (300/710 Å) or Ti/Pt/Au (200/200/2600 Å) layers may be deposited via conventional electron beam evaporation onto a GaN substrate and then may be thermally annealed at an appropriate temperature and time (about 900 deg C. for about 30 sec.) using a rapid thermal annealing technique.

Initially, hydrogen gas molecules ($H_2$) are adsorbed onto a metallic gate-electrode from the surrounding ambient environment. The adsorbed molecules are altered, such as by being catalytically dissociated from each other on a molecular or atomic level. For hydrogen gas ($H_2$), the molecules ($H_2$) are dissociated into individual hydrogen atoms (H). Next, the atomic hydrogen (H) diffuses through the metallic gate-electrode to the interface at the semiconductor surface 12. The diffusion forms a dipole layer that electrically alters the Schottky barrier (height) of the Schottky/GaN interface. In one embodiment, the barrier height may be monitored electrically such as by applying a constant voltage or bias through the diode while monitoring the current across the diode. In another embodiment, the barrier height may be monitored by maintaining a constant current through the diode and observing as a change in voltage. The magnitude of change in the Schottky barrier height increases as a gas concentration increases, and may thereby be used to determine gas concentration quantitatively. Many individual gases containing hydrogen, such as, but not limited to, amines, mercaptans, hydrocarbons, and alcohols, may be detected in this manner by the sensor device 10.

GaN and SiC gas sensor devices 10 avoid the development of surface states due to the very slow nature of their oxidation processes, thereby increasing their response stability over time. This makes these semiconductor materials ideal for the continuous monitoring of concentrations of hydrogen or hydrogen-bearing compounds, and/or oxygen or oxygen-bearing compounds. Additionally, by using various metals for the gate-electrodes 16, 18, 20, the sensitivity to a combination of gases is also possible, thereby providing for the real time monitoring of a complex environment, such as a transformer oil reservoir.

Figure 2:
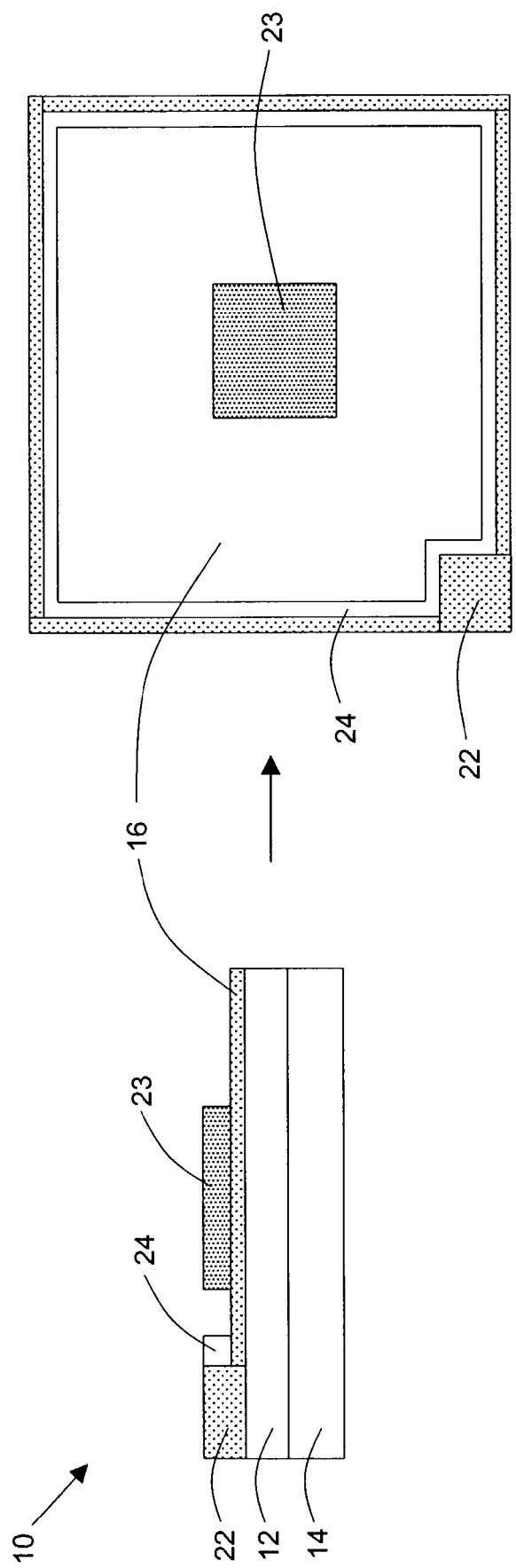
FIG. 2 is a schematic diagram illustrating a gas sensor device comprising one Schottky contact in accordance with an exemplary embodiment of the present invention.

Referring now to FIG. 2, an additional schematic diagram and cross-section of the sensor device 10 is illustrated. The sensor device 10 makes use of at least one gate-electrode (Schottky contact) 16 and one ohmic contact 22. A bond metal 23 serves to make electrical contact from a wire to the catalytic metal 16, or Schottky contact 16. As stated above, the semiconductor layer 12 may be any n-type, p-type or intrinsically doped GaN, AlN, AlGaN, AlInGaN, or SiC. The semiconductor layer 12 may be within a range of about 500 nm to several microns in thickness and is grown on a substrate 14. The sensor device 10 comprises at least one metal electrode (Ti for n-type, Pt for p-type and Al for both if so desired) for ohmic contact to the device for monitoring the electrical properties of the sensor device 10. The geometry of the sensor device 10 is such that the gate-electrode 16 and ohmic contact 22 are disposed in close proximity for increased sensitivity, preferably within about 2 microns to about 1 mm. An oxide passivation layer 24 may be applied to the surface of the sensor device 10 to passivate any dangling bonds at the surface and reduce leakage currents. The sensor device 10 may comprise a cover layer or may be disposed in a space behind a membrane, where the cover layer or membrane serve for protection or gas filtering to modify the concentration of reactant gases. An array of sensor devices 10 may be used, each with a different cover layer or membrane that responds in a different manner to a different gas.

Figure 3:
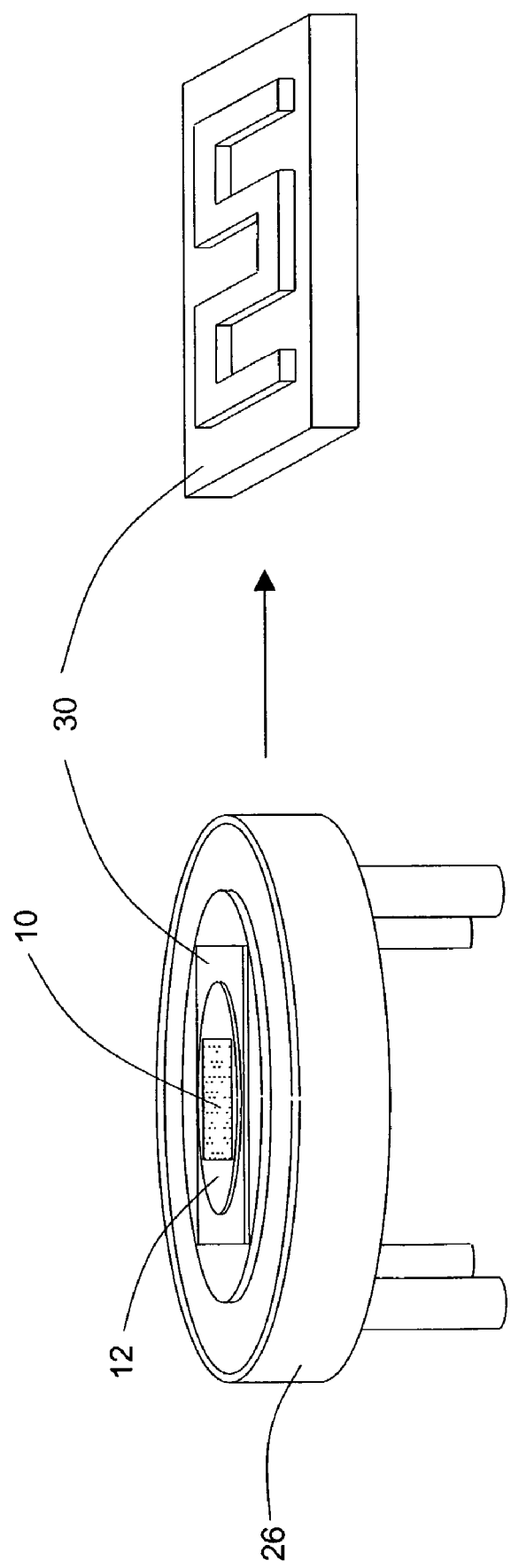
FIG. 3 is an illustration of packaging for the multi-gas sensor device of FIG. 1 in accordance with an exemplary embodiment of the present invention.

Referring now to FIG. 3, an illustration of the packaging of the sensor device 10 is shown. A packaging body 26 houses the sensor device 10, semiconductor layer 12 and heating element resistors disposed around the device 10 on the epilayer, or underneath the semiconductor chip 30. The heating element resistors may be used for generating faster response times, with the addition of heat to the surface of the sensor. Here, dissociated gas species that cause a response, are provided with thermal energy via the heating. This decreases their residency time on the surface, and thus a faster response from the sensor. In another embodiment, the sensor device 10 itself may be the heating element whereby a large current is passed through the device 10 in order to heat it to a temperature of about 150 deg C. Optionally, other heating elements such as a metal layer disposed underneath the sensor device 10 or a thermoelectric heater 30 disposed either underneath or on the side of the sensor device 10 may be used. The GaN or SiC materials used for the semiconductor layer 12 are able to withstand temperatures over about 450 deg C. without experiencing degradation. The operation of the sensor device 10 at temperatures of about 200 deg C. and above generally results in faster responses (sensitivity) to various gases.

Figure 4:
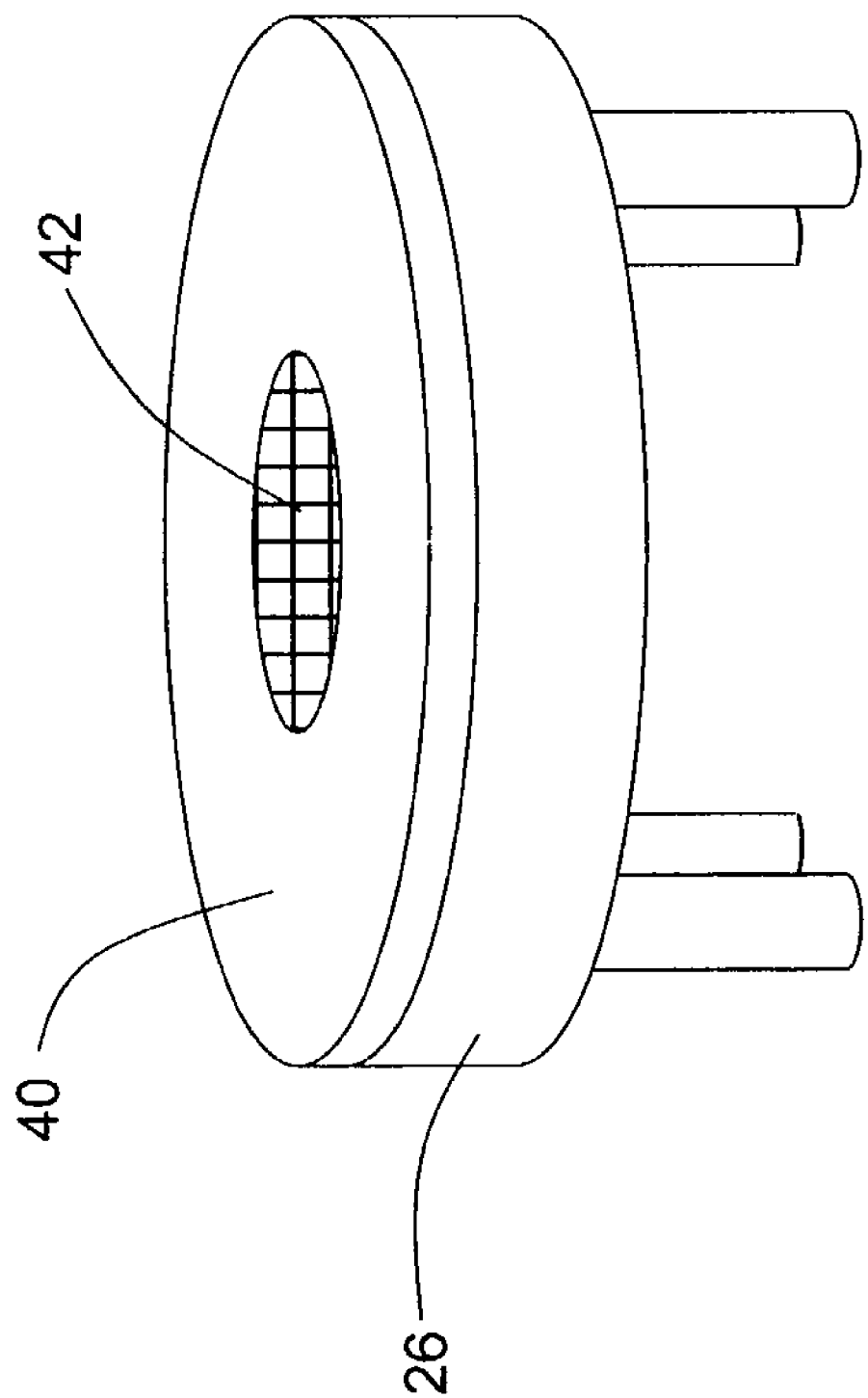
FIG. 4 is an illustration of packaging for the multi-gas sensor device of FIG. 3 further comprising a protective gate or membrane material in accordance with an exemplary embodiment of the present invention.

Referring now to FIG. 4, an illustration of the sensor packaging way comprise a header and lid assembly 40. The header and lid assembly 40 maybe soldered, resistance welded, or epoxied to facilitate a hermetic seal. A hole may then be drilled through the lid end a thin film 42 may be applied across the assembly 40 to permit the passage of only specifically chosen atoms or molecules to the surface of the sensor device 10. In one embodiment, TEFLON material may be held in the lid mechanically using pins or other fastening mechanisms. In another embodiment, KAPTON material may be epoxied around sealed edges of the lid. In yet another embodiment, a film of diamond like carbon may be deposited on the lid of the package to provide a corrosion-resistant hermetic seal. Packaging techniques in which arrays of sensor devices comprise different membrane materials provide for selectivity among various gases.

Figure 5:
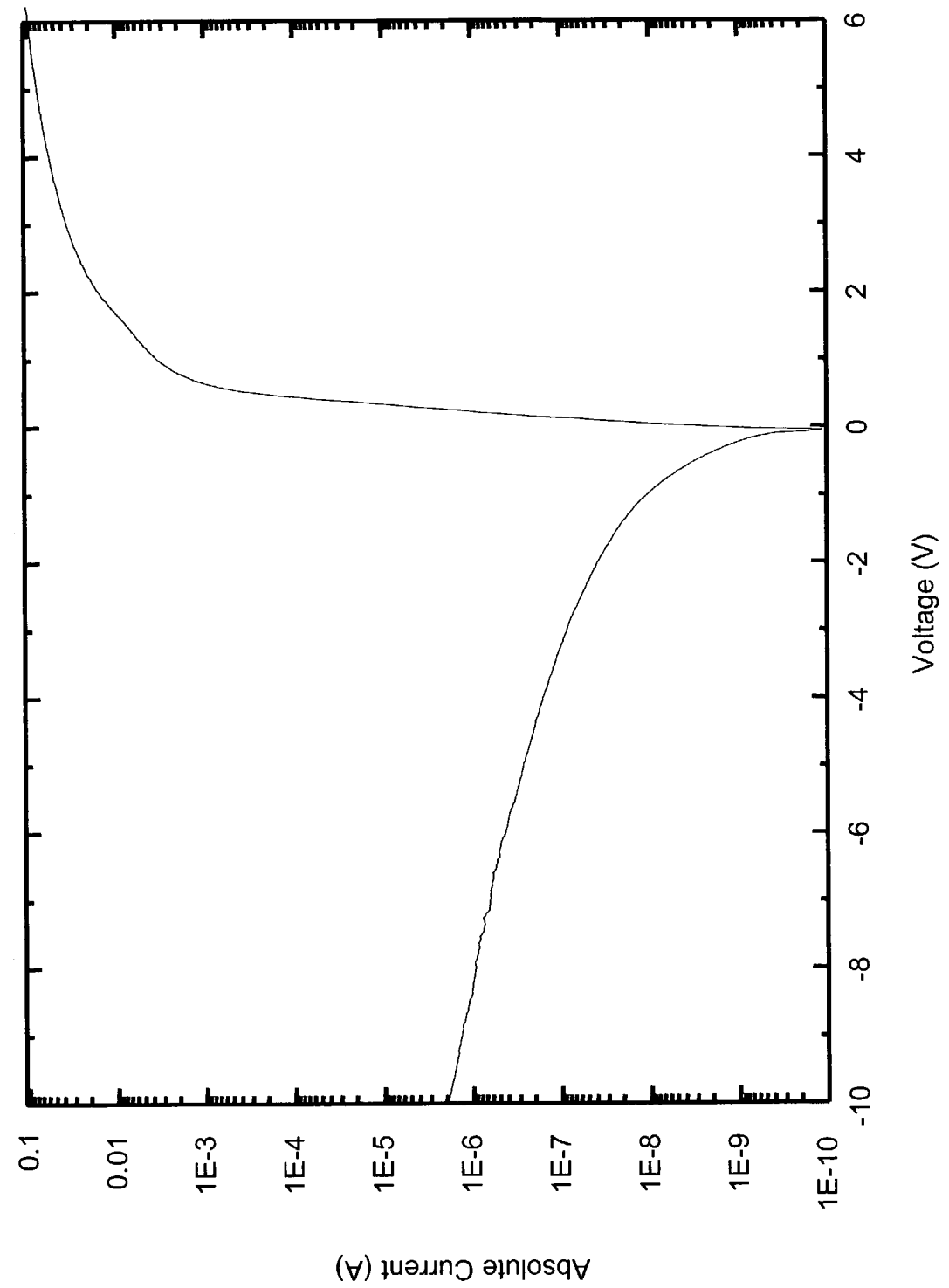
FIG. 5 is a graph illustrating current vs. Voltage characteristics of the multi-gas sensor device of FIG. 1 in accordance with an exemplary embodiment of the present invention.

Referring now to FIG. 5, the current-voltage (I-V) characteristics of the gas sensor device 10 are shown in a logarithmic plot. Here, the device behavior indicates that in reverse bias, the leakage current is approximately 1 micro-amp at negative 10 volts, while in forward bias, the current quickly attains levels in the milliamps or higher. The most important feature of this figure is the sharp increase in current from approximately 0 to 1 volt. As the device may be operated in or near this voltage range, the sharper the increase, the higher the sensitivity the sensor will have to gases.

Figure 6:
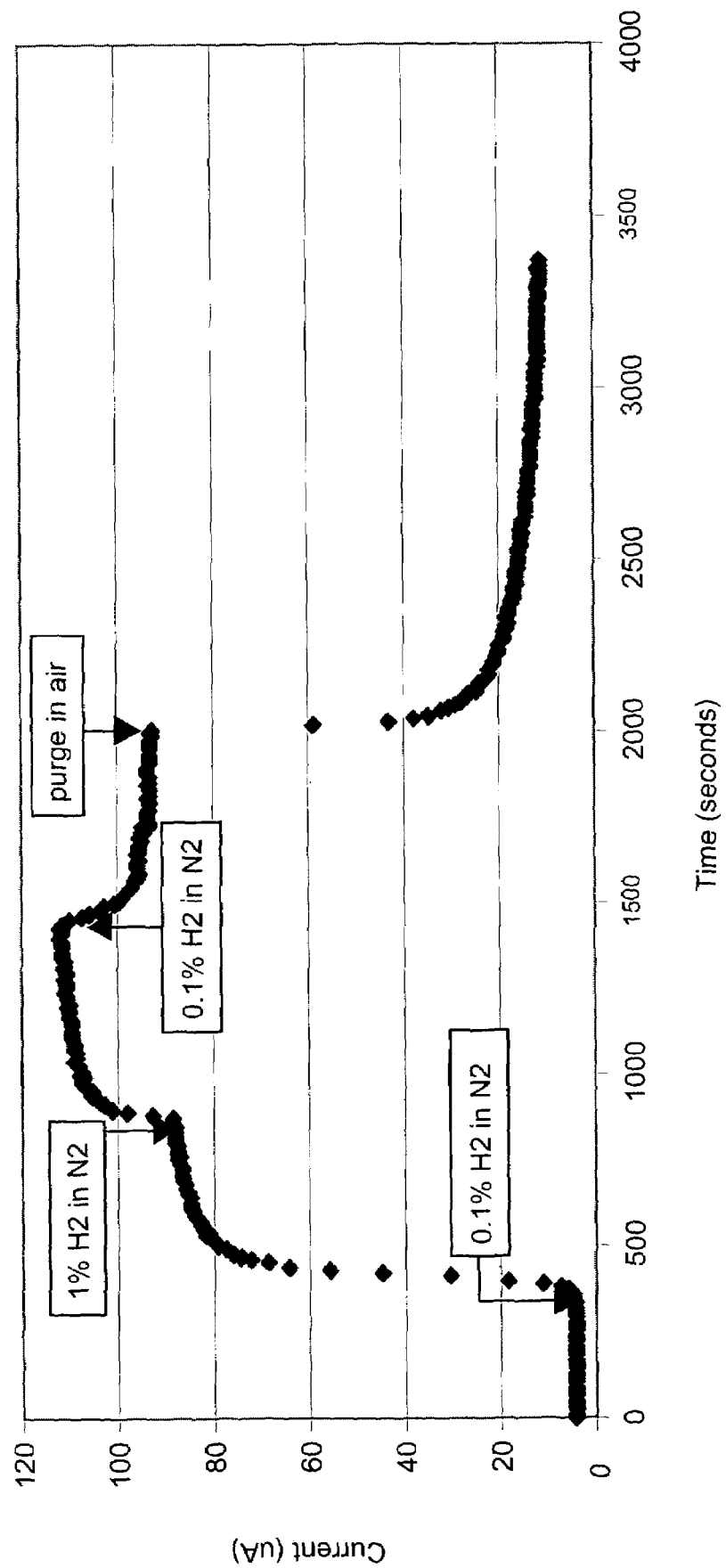
FIG. 6 is a graph illustrating the response to various concentrations of hydrogen as a function of time in accordance with an exemplary embodiment of the present invention.

Referring now to FIG. 6, the responses (current) of the gas sensor device 10 to various concentrations of hydrogen as a function of time are shown. FIG. 5 highlights the strong response of the sensor device 10 to hydrogen as operated. This data also shows that once the gas concentrations are lowered (e.g. from 1% $H_2$ to 0.1% $H_2$), the current in the device follows that trend. Although this figure illustrates the response of a gas sensing diode operated in the constant voltage mode, it may also be operated in the constant current mode. In this case, a designated current level is applied to the diode, and the resulting voltage is measured. This method also has the advantage that as the current is held constant throughout the measurement, so is the internal (resistive) heating level. Thus, the epitaxial layers (and surface) see the same heating during the range of gases exposed, which is converse to the constant-voltage method of measurement.

In the FET type device of the present invention, the FET structure is a natural amplifier, i.e. a small change in the Schottky potential may cause large changes in the channel current, which makes the sensor device 10 more sensitive. By using a silicon nitride ($Si_3N_4$) passivation layer, the sensor device may mitigate effects of surface states that may potentially cause false signals due to an interaction of the surface states with positive ions other than hydrogen. The $Si_3N_4$ layer thereby increases the selectivity to hydrogen as the hydrogen interacts with the semiconductor layer by diffusing through the metallic gate, whereas the other large molecules are prevented from interacting with the surface. Further improvements to sensitivity may be accomplished by adding a TEFLON or KAPTON cover to the sensor device 10. Some variations of TEFLON material has a selectivity of about 10:1 for $H_2$:$O_2$ or greater, which provides increased sensitivity. KAPTON material's selective porosity is even greater, near 20:1. The TEFLON or KAPTON cover may be used to filter gas compounds from a main cell in an extraction cell for increased gas concentrations.

There are several methods for which measurement data may be extracted from the described sensor embodiments. These include measuring a sensor's electrical current while applying a constant voltage, or measuring a voltage while applying a constant current. Additionally, the capacitance of a device may also be measured, as the capacitance is modified with gas concentration. All of these methods or combinations of them may be applied to a single, two electrode device such as a diode, capacitor, or a three electrode transistor. These or other methods also exist for extracting a simultaneous measurement of two or more gases, using the same types, or extensions of these device configurations.

To facilitate the measurement of two or more gases, an array of individual devices or a larger device incorporating multiple features may be used. These multiple features may include a large fingered device as shown in FIG. 1, whereby finger 16 is comprised of one catalytic metal, finger 18 is comprised of a second and finger 20 is comprised of a third and so on. As different catalytic metals have differing catalysis mechanisms to many gases, these may be taken advantage of in the simultaneous sensing of more than one gas species (e.g. ethylene, methane and hydrogen) to form a multi gas sensor.

In another embodiment of a multi gas sensor, one may modify the temperature of individual devices separately, or individual sections of a larger device. For example, individual heating (or cooling) elements may be used to separately and differently heat finger 16, from finger 18 from finger 20. A modification in the temperature of the surface of a finger will cause a modification in the desorption rate of reacted gas species from the surface. By measuring the rate at which each separately heated (or cooled) section or finger turns on or off may describe the gas species present. Additionally, fingers 16, 18 and 20 may be comprised of different catalytic metals that have varying responses to different gases. An algorithm may be then applied to extract information about separate gases.

It is apparent that there have been provided, in accordance with the device and methods of the present invention, a sensor device for gas-in-oil detection. Although the device of the present invention has been described with reference to preferred embodiments and examples thereof, other embodiments and examples may perform similar functions and/or achieve similar results. All such equivalent embodiments and examples are within the spirit and scope of the present invention and are intended to be covered by the following claims.

What is claimed is:

1. A gas sensor device, comprising:
    a semiconductor substrate;
    one or more catalytic metal gate-electrodes deposited on the surface of the semiconductor substrate; and
    an ohmic contact deposited on the surface of the semiconductor substrate;
    wherein the catalytic metal-gate electrode senses a gas;
    wherein the gas sensor device is immersed in electrically non-conductive oil; and, wherein the gas sensed comprises hydrocarbon gases dissolved in transformer oil.

2. The device of claim 1, wherein the semiconductor substrate is selected from the group consisting of group III, group IV and group V materials.

3. The device of claim 2, wherein the semiconductor substrate is selected from the group consisting of GaN, SiC, AlN, InN, AlGaN, InGaN and AlInGaN.

4. The device of claim 1, wherein the one or more catalytic metal gate-electrodes are selected from the group consisting of platinum, palladium, iridium, ruthenium, nickel, copper, rhodium, molybdenum, iron, cobalt, titanium, vanadium, tantalum, tungsten, chromium, manganese, gold, silver, aluminum, palladium:silver, tin, osmium, magnesium, zinc, alloys of these materials and combinations of these materials.

5. The device of claim 1, wherein the one or more catalytic metal gate-electrodes comprise a Schottky contact.

6. The device of claim 1, wherein the gases sensed are selected from the group consisting of hydrogen, hydrogen bearing gases, oxygen and oxygen-bearing gases.

7. The device of claim 1, wherein the gas sensed comprises gas-in-oil in x-ray tubes.

8. The device of claim 1, wherein the device is in an ambient environment ranging from about −40 deg C. to about 450 deg C.

9. The device of claim 1, further comprising a protective and gas filtering coating wherein the protective and gas filtering coating modifies the concentration of the gases.

10. The device of claim 9, wherein the coating comprises fluorocarbon resins, polymers of polytetrafluoroethylene, diamond like carbon or a combination of those films.

11. The device of claim 1, further comprising heating element resistors disposed adjacent to the device.

12. The device of claim 1, wherein the sensor device itself is a heating element whereby a current is passed through the device in order to heat the device to a temperature up to about 300 deg C.

13. The device of claim 1, wherein the device is selected from the group consisting of a diode structure, a capacitor and a field effect transistor.

14. A gas sensor device, comprising:
    a semiconductor substrate;
    a catalytic metal gate-electrode deposited on the semiconductor substrate;
    an ohmic contact deposited on the semiconductor substrate;
    a passivation layer; and
    a heating mechanism;
    wherein the catalytic metal-gate electrode senses a gas;
    wherein the passivation layer increases the selectivity of the device to the gas; and, wherein the gas sensed comprises a dissolved hydrocarbon gas in transformer oil.

15. The device of claim 14, wherein the passivation layer comprises silicon nitride, silicon dioxide or indium tin oxide.

16. The device of claim 14, wherein the semiconductor substrate is selected from the group consisting of group III, group IV and group V materials.

17. The device of claim 16, wherein the semiconductor substrate is selected from the group consisting of GaN, SiC, AlN, InN, AlGaN, InGaN and AlInGaN.

18. The device of claim 14, wherein the catalytic metal gate-electrode is selected from the group consisting of platinum, palladium, iridium, ruthenium, nickel, copper, rhodium, molybdenum, iron, cobalt, titanium, vanadium, tantalum, tungsten, chromium, manganese, gold, silver, aluminum, palladium:silver, tin, osmium, magnesium, zinc, alloys of these materials and combinations of these materials.

19. The device of claim 14, wherein the gas sensed comprises a gas-in-oil in x-ray tubes.

20. The device of claim 14, wherein the gas sensed is selected from the group consisting of hydrogen, hydrogen-bearing gases, oxygen and oxygen-bearing gas.

21. The device of claim 14, further comprising a protective and gas filtering coating wherein the coating modifies the concentration of the gas.

22. The device of claim 14, wherein the heating mechanism is selected from the group consisting of a heating resistor, a heating layer and a thermoelectric heater.

23. A method for sensing various gases, comprising:
    providing a sensor device, the sensor device comprising:
    a semiconductor substrate;
    one or more catalytic metal gate-electrodes deposited on the surface of the semiconductor substrate, wherein each of the one or more catalytic metal gate-electrodes is operable for sensing a different gas; and
    an ohmic contact deposited on the surface of the semiconductor substrate;
    immersing the sensor device in an oil-filled environment;
    allowing the oil-filled environment to interact with the one or more catalytic metal gate-electrodes;
    altering the various gases as they contact the catalytic metal gate-electrodes, the altering comprising at least one of atomically and molecularly altering chemical structure of the various gases; and altering a response of the sensor device.

24. The method of claim 23, further comprising selecting the semiconductor substrate from the group consisting of GaN, SiC, AlN, InN, AlGaN, InGaN and AlInGaN.

25. The method of claim 23, further comprising selecting the catalytic metal gate-electrode from the group consisting of platinum, palladium, iridium, ruthenium, nickel, copper, rhodium, molybdenum, iron, cobalt, titanium, vanadium, tantalum, tungsten, chromium, manganese, gold, silver, aluminum, palladium:silver, tin, osmium, magnesium, zinc, alloys of these materials and combinations of these materials.

26. The method of claim 23, wherein the gases sensed are selected from the group consisting of hydrogen, hydrogen-bearing gases, oxygen and oxygen-bearing gases.

27. The method of claim 23, wherein the method is used in the detection of dissolved hydrocarbon gases in transformer oil.

28. The method of claim 23, wherein the sensor device is operable for the detection of gas-in-oil in x-ray tubes.

29. The method of claim 25, wherein the sensor device is operable in an ambient environment ranging from about −40 deg C. to about 450 deg C.

30. The method of claim 23, wherein the sensor device further comprises a coating operable for protection and gas filtering in order to modify the concentration of the gases.

31. The method of claim 30, wherein the coating may be comprised of fluorocarbon resins, polymers of polytetrafluoroethylene, diamond like carbon or a combination of those films.

32. A method for sensing gas in an oil-filled reservoir of electrical equipment, comprising:
   providing a sensor device, the sensor device comprising:
   a semiconductor substrate;
   one or more catalytic metal gate-electrodes deposited on the surface of the semiconductor substrate, wherein each of the one or more catalytic metal gate-electrodes is operable for sensing a different gas;
   an ohmic contact deposited on the surface of the semiconductor substrate;
   a passivation layer operable for increasing the selectivity of the device to the gas; and a heating mechanism;
   immersing the sensor device in the oil-filled reservoir;
   allowing the oil to interact with the one or more catalytic metal gate-electrodes;
   altering the gas as it contacts the catalytic metal gate-electrodes, the altering comprising at least one of atomically and molecularly altering chemical structure of the gas; and
   altering a response of the sensor device.

33. The method of claim 32, wherein the sensor device further comprises a coating operable for protection and gas filtering in order to modify the concentration of the gas.

34. A method for sensing gas in an oil-filled reservoir of electrical equipment, comprising:
   providing a sensor device, the sensor device comprising:
   a semiconductor substrate;
   one or more catalytic metal gate-electrodes deposited on the surface of the semiconductor substrate, wherein each of the one or more catalytic metal gate-electrodes is operable for sensing a different gas;
   an ohmic contact deposited on the surface of the semiconductor substrate;
   a passivation layer operable for increasing the selectivity of the device to the gas;
   a protective gate material which is porous to selected gases, and
   a heating element;
   immersing the sensor device in the oil-filled reservoir;
   allowing a selectively porous membrane material to allow only oil emitted gases to interact with the sensor;
   altering the gas as it contacts the catalytic metal gate-electrodes, the altering comprising at least one of atomically and molecularly altering chemical structure of the gas; and altering a response of the sensor device.

* * * * *